(12) United States Patent
Ferree

(10) Patent No.: US 8,337,528 B2
(45) Date of Patent: Dec. 25, 2012

(54) METHODS AND APPARATUS FOR STABILIZING A SPINAL SEGMENT

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 1322 days.

(21) Appl. No.: 11/946,001

(22) Filed: Nov. 27, 2007

(65) Prior Publication Data

US 2008/0140123 A1    Jun. 12, 2008

Related U.S. Application Data

(60) Provisional application No. 60/861,499, filed on Nov. 28, 2006.

(51) Int. Cl.
*A61B 17/88* (2006.01)
(52) U.S. Cl. .................. 606/279; 606/263; 623/17.11
(58) Field of Classification Search .............. 606/60, 606/246, 263, 279, 280, 70–71, 281, 283–286, 606/300–301, 228, 232, 74, 103, 151–156; 623/17.11–17.16, 13.13–13.14
See application file for complete search history.

(56) References Cited

U.S. PATENT DOCUMENTS

| | | | |
|---|---|---|---|
| 3,997,138 A | 12/1976 | Crock et al. |
| 4,146,022 A | 3/1979 | Johnson et al. |
| 4,854,304 A | 8/1989 | Zielke |
| 4,966,600 A | 10/1990 | Songer et al. |
| 5,092,867 A | 3/1992 | Harms et al. |
| 5,108,397 A | 4/1992 | White |
| 5,342,361 A | 8/1994 | Yuan et al. |
| 5,352,224 A | 10/1994 | Westermann |
| 5,387,213 A | 2/1995 | Breard et al. |
| 5,423,820 A | 6/1995 | Miller et al. |
| 5,496,318 A | 3/1996 | Howland et al. |
| 5,611,801 A | 3/1997 | Songer |
| 5,702,399 A | 12/1997 | Kilpela et al. |
| 5,704,936 A | 1/1998 | Mazel |
| 5,725,582 A | 3/1998 | Bevan et al. |
| 5,782,831 A | 7/1998 | Sherman et al. |
| 5,904,682 A | 5/1999 | Rogozinski |
| RE36,221 E | 6/1999 | Breard et al. |
| 5,964,769 A | 10/1999 | Wagner et al. |
| 5,989,256 A | 11/1999 | Kuslich et al. |
| 5,993,448 A | 11/1999 | Remmler |
| 5,997,542 A | 12/1999 | Burke |
| 6,033,429 A | 3/2000 | Magovern |

(Continued)

*Primary Examiner* — Alvin Stewart
*Assistant Examiner* — Michelle C Eckman
(74) *Attorney, Agent, or Firm* — Pandiscio & Pandiscio

(57) ABSTRACT

One or more sutures can be used in spinal applications to hold an intradiscal device in place between two vertebrae or repair a defect in the soft tissue of the spine, such as the annulus fibrosis or the dura. Tension can also be applied to the sutures to stabilize a spinal segment having an intradiscal device to prevent or minimize excessive spinal extension, lateral bending, and axial rotation of the spinal segment. Anchors are placed in two adjacent vertebrae and sutures are passed through each anchor. The sutures can be passed through portions of the intradiscal device. Alternatively, the sutures can be passed through a mesh patch which is held against the vertebrae to hold the intradiscal device in place. Tension is applied to the first and second ends of the sutures and the sutures are welded together. The sutures can be welded in a cross-braced arrangement minimize or prevent extension, lateral bending, and rotation of the spinal segment. For example, the sutures can be welded in a diagonal pattern, a horizontal pattern, a vertical pattern or any combination thereof across the adjacent vertebrae.

13 Claims, 11 Drawing Sheets

U.S. PATENT DOCUMENTS

| | | | |
|---|---|---|---|
| 6,093,205 A * | 7/2000 | McLeod et al. | 623/17.16 |
| 6,248,106 B1 | 6/2001 | Ferree | |
| 6,287,308 B1 | 9/2001 | Betz et al. | |
| 6,296,643 B1 | 10/2001 | Hopf et al. | |
| 6,423,065 B2 | 7/2002 | Ferree | |
| 6,645,211 B2 * | 11/2003 | Magana | 606/247 |
| 6,878,167 B2 | 4/2005 | Ferree | |
| 7,090,675 B2 * | 8/2006 | Songer | 606/247 |
| 7,201,774 B2 | 4/2007 | Ferree | |
| 7,776,069 B2 * | 8/2010 | Taylor | 606/249 |
| 7,799,060 B2 | 9/2010 | Lange et al. | |
| 2001/0027319 A1 * | 10/2001 | Ferree | 606/61 |
| 2002/0120269 A1 * | 8/2002 | Lange | 606/61 |
| 2003/0195514 A1 * | 10/2003 | Trieu et al. | 606/61 |
| 2004/0039392 A1 * | 2/2004 | Trieu | 606/86 |
| 2004/0260287 A1 * | 12/2004 | Ferree | 606/61 |
| 2006/0084985 A1 * | 4/2006 | Kim | 606/61 |
| 2006/0089646 A1 * | 4/2006 | Bonutti | 606/61 |
| 2007/0005062 A1 * | 1/2007 | Lange et al. | 606/61 |
| 2007/0073293 A1 * | 3/2007 | Martz et al. | 606/61 |
| 2007/0168035 A1 * | 7/2007 | Koske | 623/17.13 |
| 2007/0239158 A1 * | 10/2007 | Trieu et al. | 606/61 |
| 2008/0125779 A1 | 5/2008 | Ferree | |
| 2008/0195151 A1 | 8/2008 | Ferree | |
| 2008/0262550 A1 * | 10/2008 | Ferree | 606/263 |
| 2010/0076492 A1 * | 3/2010 | Warner et al. | 606/279 |
| 2010/0152779 A1 * | 6/2010 | Allard et al. | 606/279 |
| 2010/0211108 A1 * | 8/2010 | Lemole, Jr. | 606/264 |

* cited by examiner

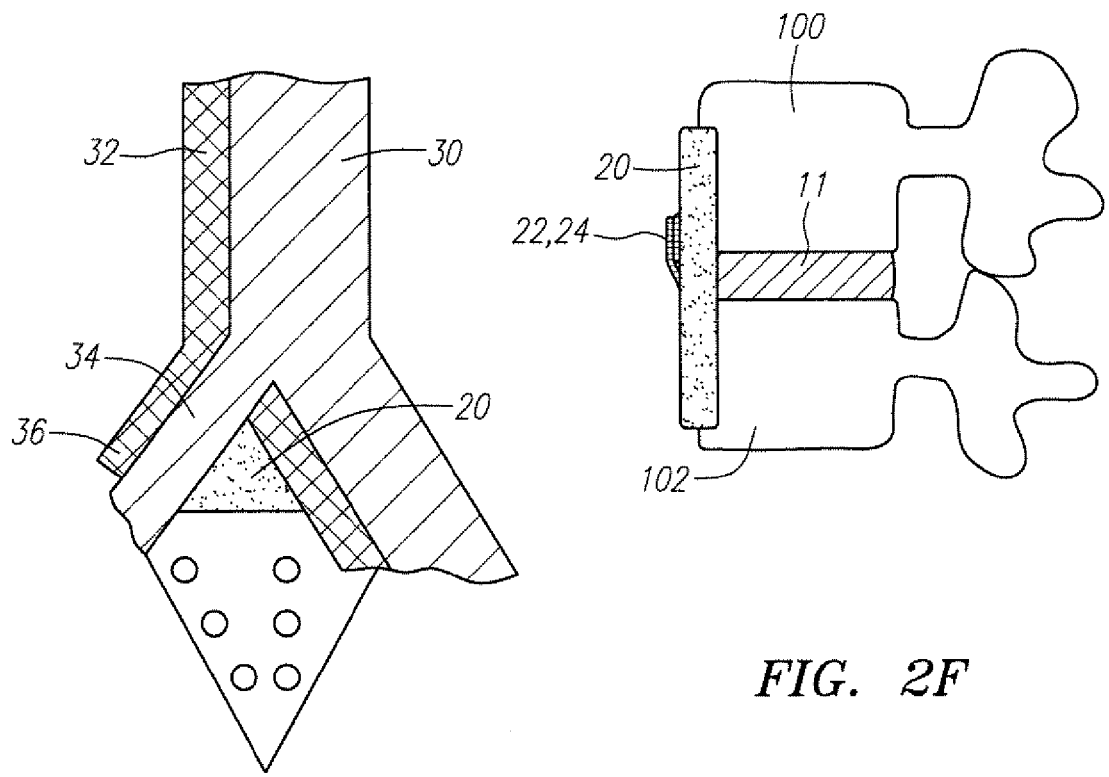
FIG. 2F
FIG. 2E
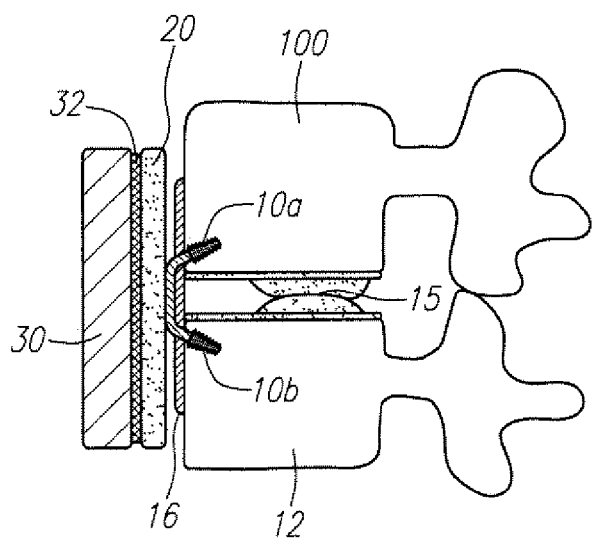
FIG. 2G
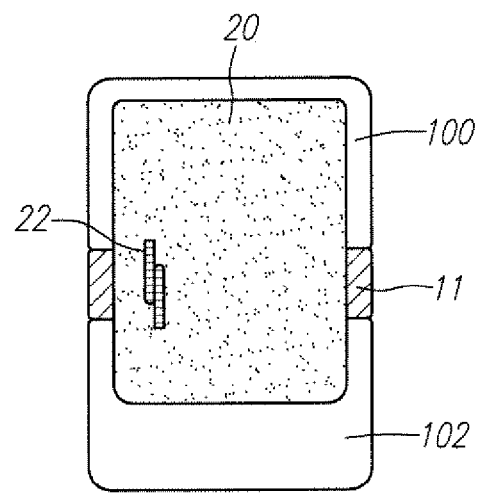
FIG. 2H

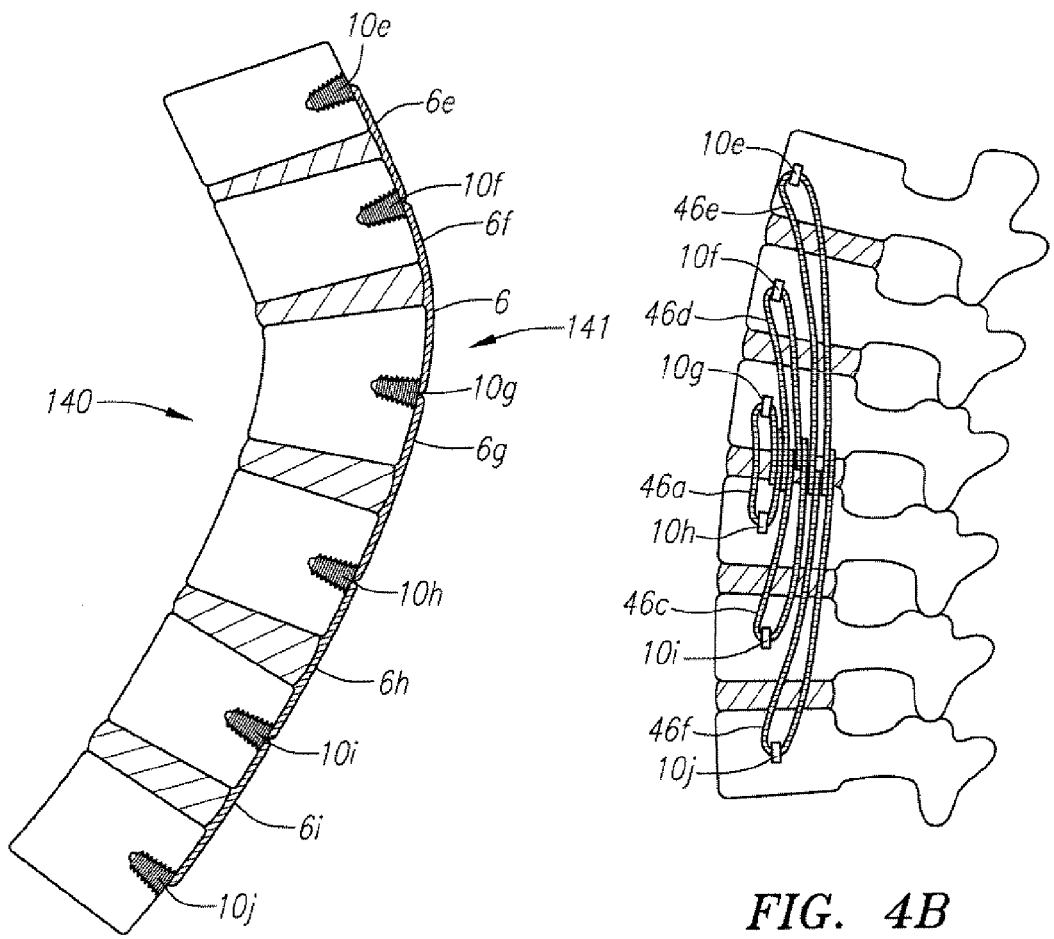
FIG. 4A
FIG. 4B
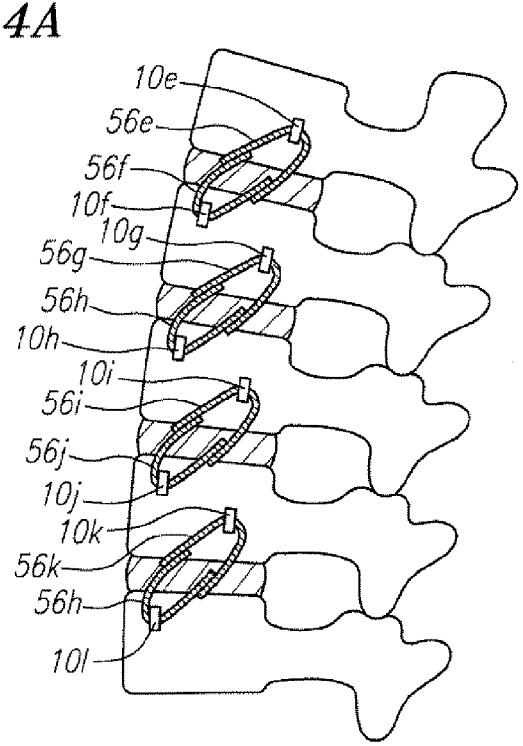
FIG. 4C

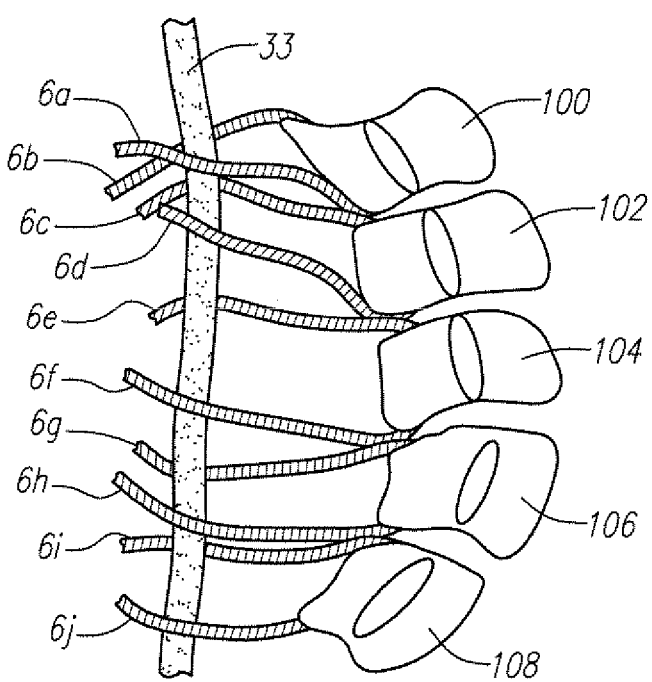 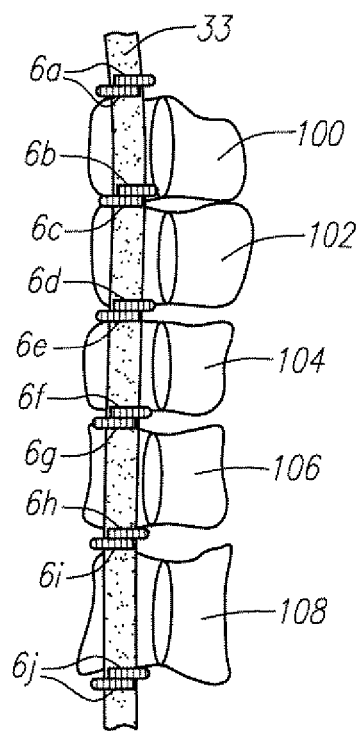
FIG. 6A    FIG. 6B
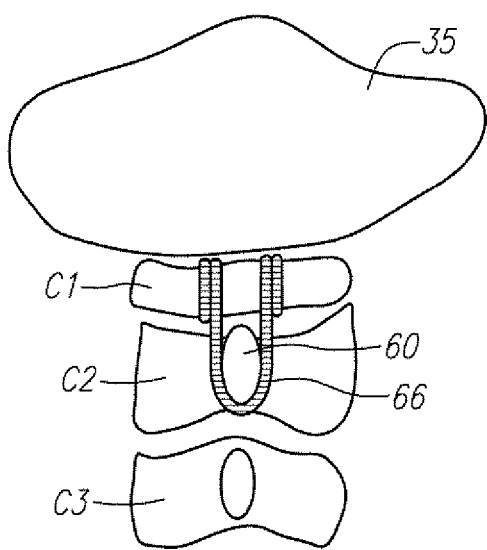 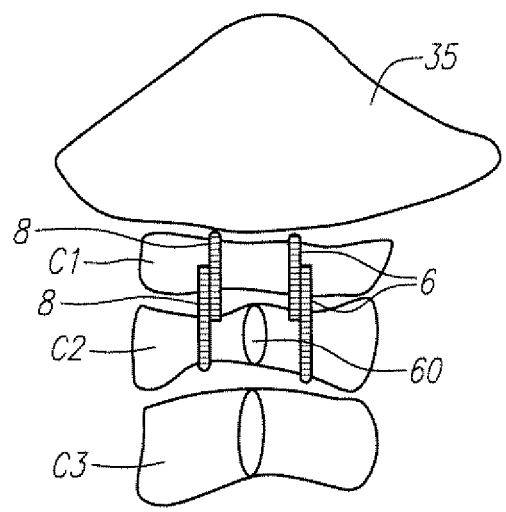
FIG. 7A    FIG. 7B

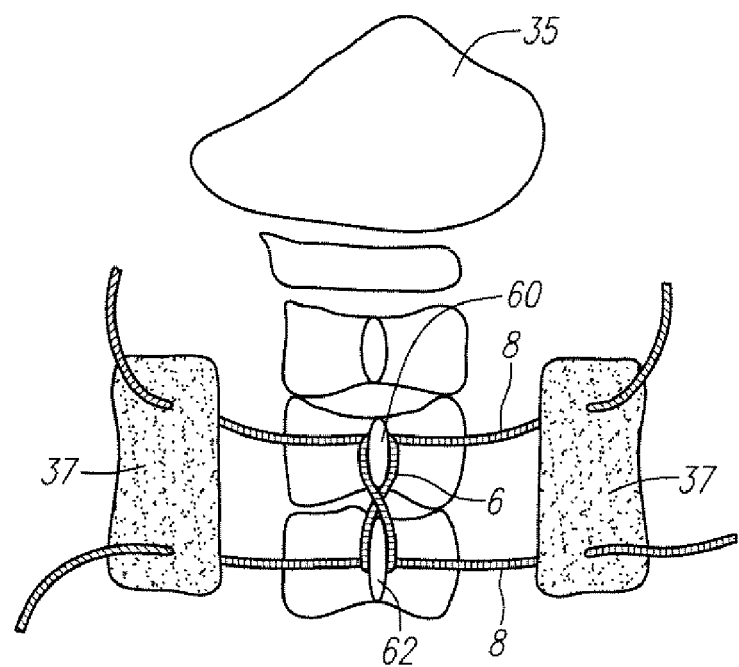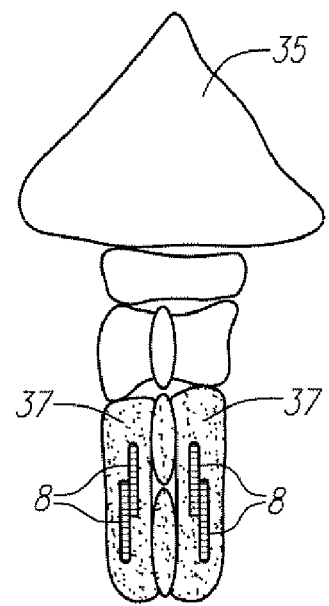
FIG. 8A  FIG. 8B
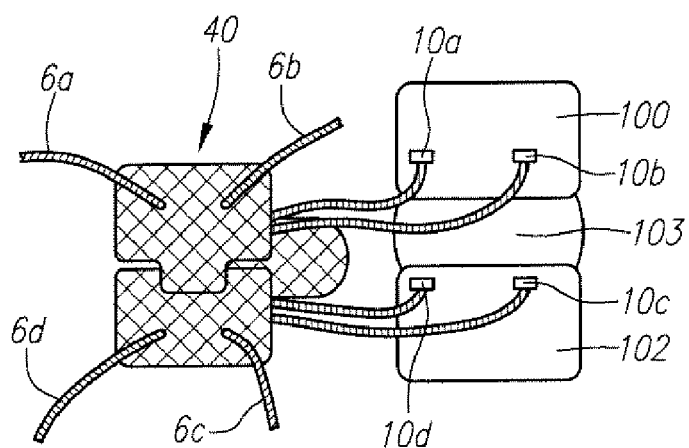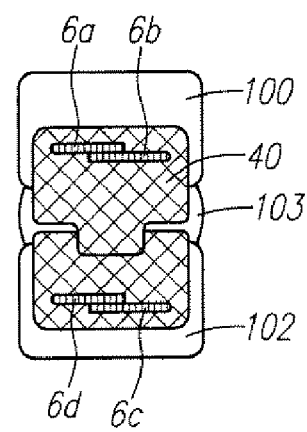
FIG. 9A  FIG. 9B

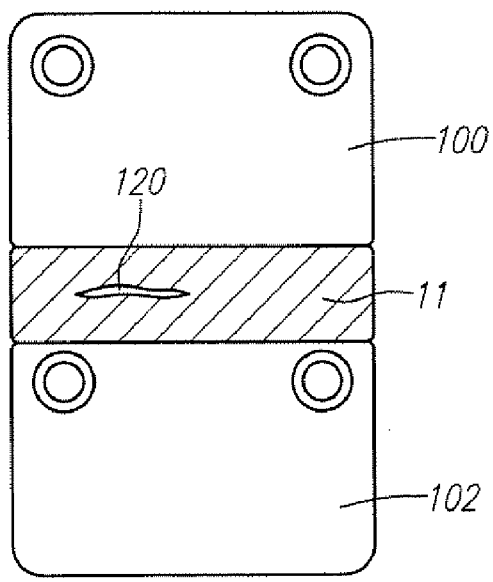
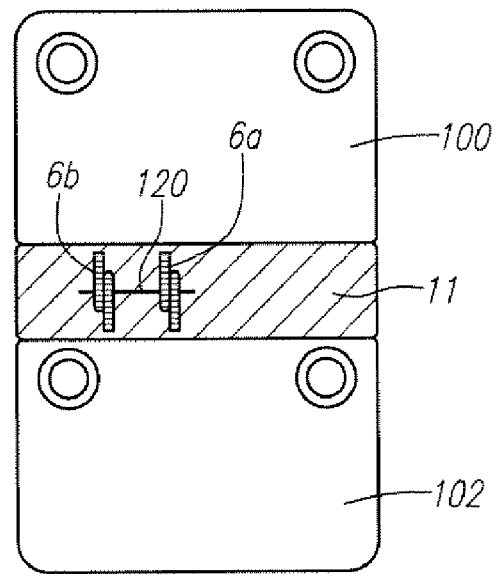
FIG. 11A  FIG. 11B
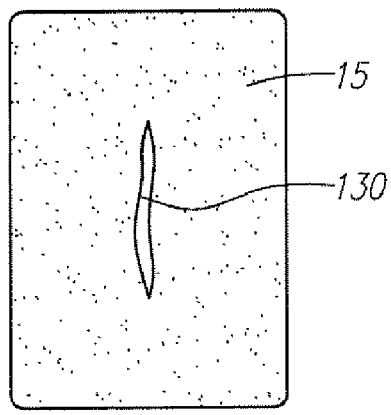
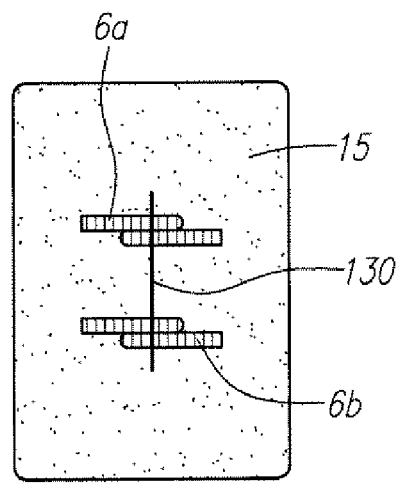
FIG. 12A  FIG. 12B

METHODS AND APPARATUS FOR STABILIZING A SPINAL SEGMENT

RELATED APPLICATIONS

This application claims the benefit of provisional application 60/861,499, filed Nov. 28, 2006, entitled "Annulus and Spinal Ligament Reconstruction." This application is related to co-pending application 60/808,795, filed May 26, 2006, entitled "Fastening Assemblies for Disc Herniation Repair and Methods of Use." The application is also related to U.S. Pat. Nos. 6,248,106 and 6,423,065. All of the above-referenced patent and applications are hereby expressly incorporated by reference in their entirety.

FIELD OF THE INVENTION

The subject invention resides in methods and apparatus for reconstructing the annulus fibrosis (AF) of a spinal disc and the ligaments of the spine. The invention is particularly well suited to the repair of defects in the annulus fibrosis and prevention of extrusion of material or devices placed into the disc space and to the prevention of excessive spinal motion.

BACKGROUND

The human intervertebral disc is an oval to kidney bean-shaped structure of variable size depending on the location in the spine. The outer portion of the disc is known as the annulus fibrosis (AF). The annulus fibrosis is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The annulus fibrosis contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the annulus fibrosis. As discussed in co-pending U.S. patent application Ser. No. 10/407,554 and U.S. Pat. No. 6,878,167, the content of each being expressly incorporated herein by reference in their entirety, the posterior portion of the annulus fibrosis has abundant pain fibers.

Herniated nucleus pulposus (HNP) occurs from tears in the annulus fibrosis. The herniated nucleus pulposus often allies pressure on the nerves or spinal cord. Compressed nerves cause back and leg or arm pain. Although a patients symptoms result primarily from pressure by the nucleus pulposus, the primary pathology lies in the annulus fibrosis.

Surgery for herniated nucleus pulposus, known as microlumbar discectomy (MLD), only addresses the nucleus pulposus. The opening in the annulus fibrosis is enlarged during surgery, further weakening the annulus fibrosis. Surgeons also remove generous amounts of the nucleus pulposus to reduce the risk of extruding additional pieces of nucleus pulposus through the defect in the annulus fibrosis. Although microlumbar discectomy decreases or eliminates a patient's leg or arm pain, the procedure damages weakened discs.

Suture anchor and knotless suture fastening technology have been used extensively to repair soft tissues about the knee and shoulder. The sutures are used to attach the soft tissues to the bones that form the joints. The anchor is embedded in the bone. The ends of the suture are then passed through the tendon, such as the rotator cuff of the shoulder and fastened to one another. Recessing the suture welds in the soft tissue over the bone prevents friction between the suture and the bone and prevents the ends of the sutures from catching on adjacent tissues and thus peeling the weld apart.

Suture anchors eliminate the laborious method of threading sutures through holes drilled into bones. The use of a weld is better than the use of knots in the prior art because knots are difficult to tie during arthroscopic procedures and slip several millimeters allowing the soft tissues within the suture to migrate away from the bone. However, such technology has rarely been used for reconstructive spinal procedures. Suture based spinal devices would be exposed to substantially higher loads, more friction, and must work longer than such devices are exposed to in the shoulder. In spinal applications, the sutures, including the welded portion of the sutures would lie directly against the vertebrae of the spinal device and thus would be subjected to more friction than sutures and welds of a device connecting bone and soft tissue. Moreover, the high profile of the sutures and especially the suture welds not recessed within soft tissue would increase the excessive wear on the sutures and the risk of peeling the suture welds apart.

SUMMARY

During insertion of an intradiscal device, a portion of the annulus fibrosis and a portion of the ligaments of the spine are excised to allow insertion of materials and devices into the disc space. For example, a portion of the anterior half of the annulus fibrosis and a portion of the anterior longitudinal ligament (ALL) are excised to enable insertion of bone growth promoting materials and fusion devices in interbody fusion procedures. A portion of the annulus fibrosis and a portion of the anterior longitudinal ligament are also excised to enable insertion of motion preserving devices into the disc. For example, Total Disc Replacements (TDRs) and Nucleus Replacements (NRs) are often inserted through the anterior portion of discs.

Removal of portions of the annulus fibrosis and anterior longitudinal ligament increase the flexibility of the spine and allow excessive motion of the spine. For example, removal of the tissues mentioned permits excessive spinal extension, lateral bending, and axial rotation. Destabilizing the spine decreases the chance of a successful fusion for an interbody fusion procedure. Destabilizing the spine following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The present invention provides methods for using sutures in spinal applications to stabilize a spinal segment and/or hold an intradiscal device in place without passing the sutures through soft tissue. The invention can be used to prevent or minimize excessive spinal extension, lateral bending, and axial rotation.

In one embodiment, anchors are placed in two adjacent vertebrae and sutures are passed through each anchor. The first end of one suture extending from the anchor in the cranial vertebra is welded to the first end of a second suture extending from the anchor in the caudal vertebrae. Tension is applied to second ends of the first and second sutures and the second ends are welded together.

In some embodiments, two or more anchors can be used in each vertebrae and the sutures may be welded in a cross-braced arrangement minimize or prevent extension, lateral bending, and rotation of the spinal segment. For example, the sutures can be welded in a diagonal pattern, a horizontal pattern, a vertical pattern or any combination thereof across the adjacent vertebrae. Tension can be applied across the sutures prior to welding to provide compression across the disc space between the adjacent vertebrae. In other embodiments, two or more sutures may be threaded through each anchor to provide additional tension and compression across the spinal segment.

In some embodiments, a mesh patch can be placed between the sutures and the vertebrae to provide a cushion between the sutures and the bone and reduce friction on the sutures and the suture welds. In some embodiments, the material for the mesh can be selected such that connective tissue will grow into and over the mesh in vivo, forming a synthetic tendon-like layer that further cushions and protects the sutures. In some embodiments, an anti-adhesion patch can be placed over the exposed portions if the sutures and the suture anchors to protect the suture welds from friction with adjacent structures that could create peeling forces and pull the suture welds apart as well as to protect the adjacent structures from the stiff ends of the suture welds.

The invention may also be used to tether the spine. Tethering the immature spine enables correction of spinal deformities as the spine grows. The invention may incorporate materials that encourage the growth of connective tissue into components of the various devices taught in the invention. The invention may also incorporate materials that prevent the growth of connective tissue into components of the various devices taught in the invention. Preventing or limiting connective in-growth may be used to diminish adhesions at the surgical site.

BRIEF DESCRIPTION OF THE DRAWINGS

FIG. 2E is an anterior view of a portion of the lumbosacral spine, a portion of the aorta, a portion of the vena cava, portions of the iliac arteries portions of the iliac veins 36, and the embodiment of the invention drawn in FIG. 2D.

FIG. 2F is a lateral view of the spine and the embodiment of the invention drawn in FIG. 2E.

FIG. 2G is a lateral view of a sagittal cross section of the spine and the embodiment of the invention drawn in FIG. 2F FIG. 2H illustrates an anterior view of the spine and an alternate embodiment of the invention drawn in FIG. 2D.

FIG. 4A illustrates an anterior view of an alternative embodiment of the invention wherein one or more sutures can be used to tether the spine.

FIG. 4B is a lateral view of the spine and the embodiment of the invention drawn in FIG. 4A.

FIG. 4C is lateral view of the spine and an alternative embodiment of the invention drawn in FIG. 4B.

FIG. 6A is a posterior view of the spine illustrating an alternative embodiment of the invention for tethering the spine wherein the sutures are passed under the lamina of the vertebrae.

FIG. 6B is a posterior view of the embodiment in FIG. 5. The ends of sutures 6 showing the sutures welded together around a spinal rod.

FIG. 7A is a posterior view of the cervical spine illustrating an embodiment of the invention in portions of the cervical spine.

FIG. 7B is a posterior view of the cervical spine illustrating an alternative embodiment of the invention in portions of the cervical spine.

FIG. 8A is a posterior view of the cervical spine illustrating an alternative embodiment of the invention in portions of the cervical spine.

FIG. 8B is a posterior view of the embodiment in FIG. 5A showing the sutures welded together over bone graft material.

FIG. 9A illustrates an alternative embodiment of the invention using one or more sutures to attach prosthetic devices to the spine.

FIG. 9B is an anterior view of a portion of the embodiment of the invention drawn in FIG. 9A showing the sutures welded together over the prosthetic device.

FIG. 11A is a posterior view of a coronal cross section of the spine through the pedicles of the vertebrae illustrating a defective region in the annulus fibrosis.

FIG. 11B illustrates an embodiment of method of using sutures to close the defect in the annulus fibrosis of FIG. 10A FIG. 12A is a posterior view of a portion of the dura. The dura has an incision, tear, or laceration.

FIG. 12B illustrates an embodiment of a method of using one or more sutures to close a defect in the spinal dura.

DETAILED DESCRIPTION

Figure 1A:
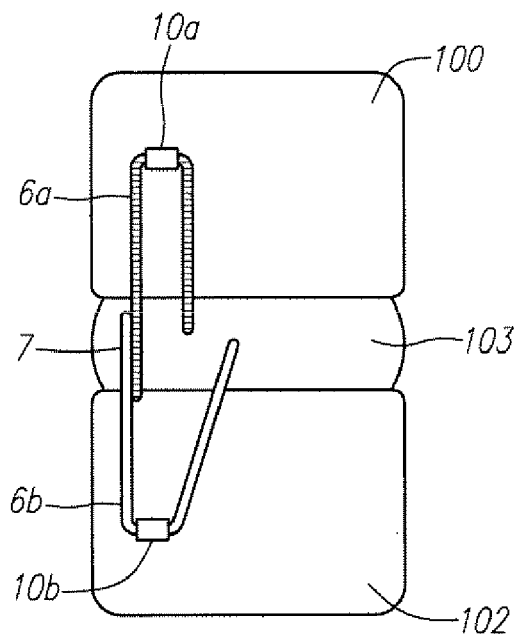
FIG. 1A illustrates an anterior view of segment of a spine with suture anchors placed in adjacent vertebrae and first ends of sutures extending from each anchor welded together.
Figure 1B:
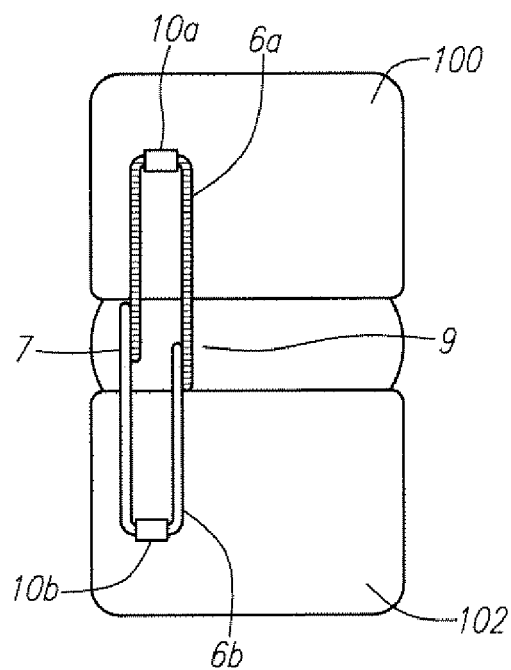
FIG. 1B illustrates an anterior view of the embodiment in FIG. 1A with second ends of the sutures welded together.
Figure 2A:
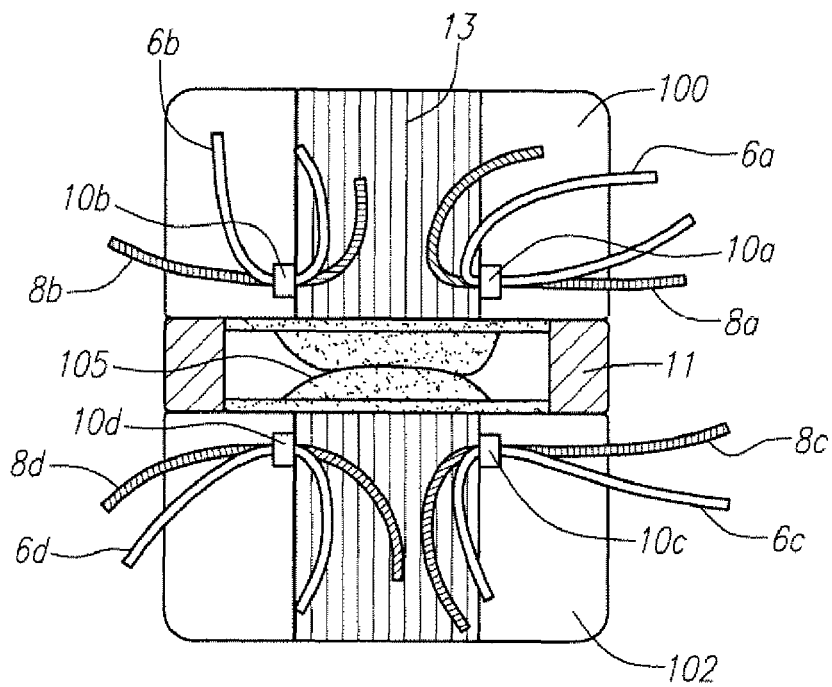
FIG. 2A illustrates an anterior view of an alternative embodiment having sutures placed in adjacent vertebrae and two sutures extending from each anchor.
Figure 2B:
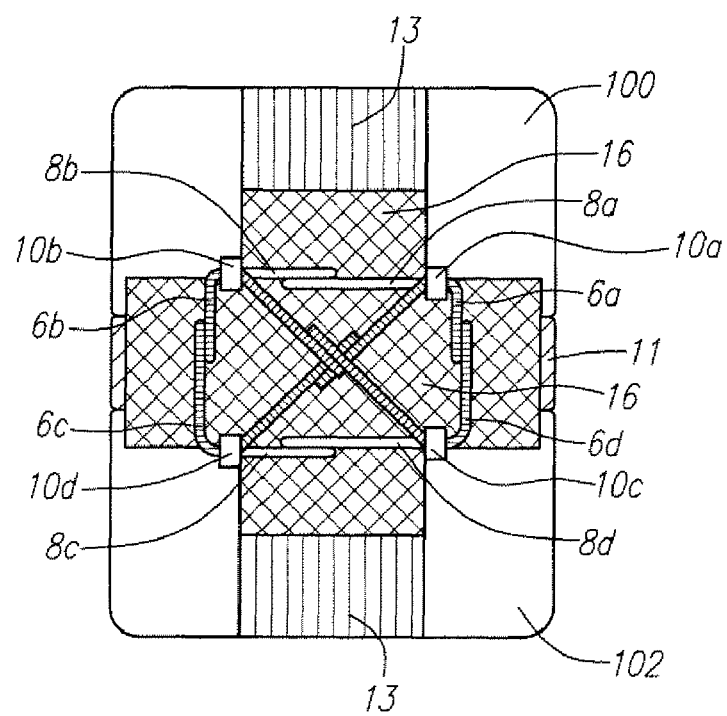
FIG. 2B illustrates an anterior view of the embodiment in FIG. 2A with the sutures welded together in a cross-braced pattern.

FIGS. 1A-1B illustrate a method using two sutures to join adjacent vertebrae. Anchors 10a and 10b are placed in vertebrae 100 and 102 respectively. Suture 6a is threaded through anchor 10a and suture 6b is threaded through anchor 10b. The sutures 6a and 6b are made of materials than can be welded together. For example, the sutures can be monofilament or multifilament configurations of nylon, polypropylene, polyester, polyethylene, or other suitable material. The sutures 6a and 6b can be different sizes and/or made of different materials As shown in FIG. 1A, the first end of one suture 6a is welded to the first end of a second suture 6b to form a suture weld 7. The weld is preferably caused by heat-generating or heat-conducting instruments. The heat may be generated ultrasonically or by other means. Next, as shown in FIG. 2B, the second ends of the two sutures 6a and 6b are welded together to form suture weld 9. During welding of the second ends of the sutures 6a, 6b, care must be taken so that the first weld 7 is not advanced into an eyelet of anchor 10a or 10b, which could result in peeling apart of the weld 7. In order to prevent the weld 7 from impinging on anchor 10a or 10b, equal tension is applied to both ends of sutures 6a, 6b. In addition, in some embodiments, both ends of the sutures can be advanced through the eyelets of the anchors, in opposite directions, to prevent impingement of a prior weld against a suture anchor. For example, after the first weld 7, if both sutures 6a,b travel through the eyelets of the anchors 10a,b in the same direction, for example clockwise, the first weld may impinge on an anchor. However, if the first suture 6a is pulled through anchor 10a in a clockwise direction and the second suture 6b is pulled through anchor 10b the same distance but in a counterclockwise direction, the first weld remains positioned between the anchors 10a,b rather than possibly impinging against an anchor.

In some embodiments, the sutures may be used to stabilize a spinal segment after a portion of the annulus fibrosis and/or a portion of the ligaments of the spine have been excised during insertion of an intradiscal device. FIG. 2A is an anterior view of the spine, a total disc replacement (TDR), and four suture anchors. The anterior portion of the annulus fibrosis 11 and the anterior longitudinal ligament 13 were excised to permit insertion of the total disc replacement (TDR) 15 into the disc space. Two suture anchors 10a, 10b were placed into the vertebra 100 cranial to the disc and two suture anchors 10c, 10d were placed into the vertebra 102 caudal to the disc. Each suture anchor 10a,b,c,d has two eyelets with first sutures 6a,b,c,d and an second sutures 8a,b,c,d passing therethrough.

As discussed above, the sutures 6a,b,c,d and 8a,b,c,d are made of materials than can be welded together. For example, the sutures can be monofilament or multifilament configurations of nylon, polypropylene, polyester, polyethylene, or other suitable material. In some embodiments, the first set of sutures 6a,b,c,d and the second set of sutures 8,a,b,c,d could be different sizes and/or made of different materials. For example, one set of sutures 6a-d could be a #5 polyester multifilament material. The other set of sutures 8a-d could be made of a #5 resorbable multifilament suture, such as Vicryl (Ethicon, N.J.). Alternatively, one set of sutures could be more elastic than the second set of sutures. For example, one set of sutures 6a-d could reversibly stretch about 1 to about 10 mm. The other set of sutures 8a-d could reversibly stretch about 5 to about 8 mm. Embodiments of the invention used in spinal fusion procedures preferably include relatively inelastic sutures.

In addition, in different embodiments, the anchors could vary in size from about 3 to about 12 mm in diameter and about 4 to about 40 mm in length. For example, anchors having a diameter of about 3 mm and a length of about 7 mm could be used in the anterior portions of cervical vertebrae. Additionally, anchors having a diameter of about 8 mm and a length of about 35 mm could be used in the anterior portions of lumber vertebrae. The anchors are preferably made of a MRI-compatible material. For example, the anchors could be made of titanium, plastic, or other material. The anchors may additionally be coated with a material, such as hydroxyappetite, that promotes the in-growth of bone. In an alternative embodiment, the anchors could be hollow and filled with a material that promotes bone in-growth.

With reference to FIG. 2B, the medial ends of the sutures 6a-d and 8a-d from the anchors are welded together in a diagonal pattern over the disc space. The lateral ends of one set of sutures 6a-d are then welded together to create vertical fixation suture arms and the lateral ends of the second set of sutures 8a-d are welded together to create horizontal fixation suture arms. Tension is applied to the sutures 6a,b,c,d and 8,a,b,c,d before the sutures 6a,b,c,d and 8,a,b,c,d are welded together. As discussed above, during subsequent welds, equal tension is applied to both ends of the sutures having a preceding suture weld to ensure that preceding suture welds are not advanced into the eyelet of anchor 10a,b,c,d which could result in peeling apart of the weld.

In an alternative embodiment, both sets of the lateral ends of the fixation sutures could have been welded to create two sets of vertical fixation suture arms (not shown). In general, the sutures can be welded in a pattern having any combination of diagonal connections, generally upper and lower horizontal connections, and/or generally left and right vertically extending connections. For example, in some embodiments, the sutures may be welded in a pattern of a FIG. 8 having both generally vertically extending fixation suture arms and diagonal fixation suture arms. In alternative embodiments, the sutures may be welded in a pattern of a quadrilateral, having generally horizontal and vertical suture arms, with diagonal suture arms extending between the vertices.

The weld is preferably caused by heat-generating or heat-conducting instruments. The heat may be generated ultrasonically or by other means. Instruments with special tips may be used to weld the sutures within deep areas of the body. For example, instruments that are about 15 to abut 45 cm in length may be needed to weld sutures in the abdomen. The welding instruments are preferably about 4 to about 8 mm in diameter.

In some embodiments, a piece of porous mesh material 16 is placed between the fixation sutures 6a-d, 8a-d and the vertebrae 100, 102. The mesh 16 acts as scaffolding for connective tissue in-growth from the annulus fibrosis 1, the anterior longitudinal ligament 13, and the vertebrae 100, 102. The mesh between the sutures 6a,b,c,d and 8a,b,c,d and the vertebrae 100 and 102, forms a synthetic tendon-like layer that cushions and protects the sutures 6a,b,c,d and 8a,b,c,d, and especially the suture welds, from damage due to the motion between the sutures 6a,b,c,d and 8a,b,c,d and the vertebrae 100 and 102. The pores within the mesh 16 are preferably about 0.1 to 2.0 mm in diameter. Mesh piece 16 may be made of synthetic materials such as polyester, polypropylene, ePTFE, or polyethylene. Alternatively, the mesh could be made of natural material such as autograft, allograft, or xenograft tissues such as acellular dermis, swine intestinal submucosa, ligaments, facia, or tendon. The mesh 16 should extend over both sides of the anterior longitudinal ligament 13 and the annulus fibrosis 11 on either side of the annular window. The connective tissue, the mesh 11, and the fixation sutures 6a,b,c,d and 8a,b,c,d at least partially reproduce the function of the annulus fibrosis and the anterior longitudinal ligament. The components also prevent extrusion of tissue that resides within the disc, such as the nucleus pulposus, or materials or devices that are placed within the disc. Radio-opaque markers could be added to the mesh and or the fixation sutures to help identify the location of the components on x-ray. For example, metal wires or staples could be included in mesh or fixation sutures. Alternatively, radio-opaque materials such as barium or other contrast agents may be used to "dye" the mesh or fixation sutures.

Figure 2C:
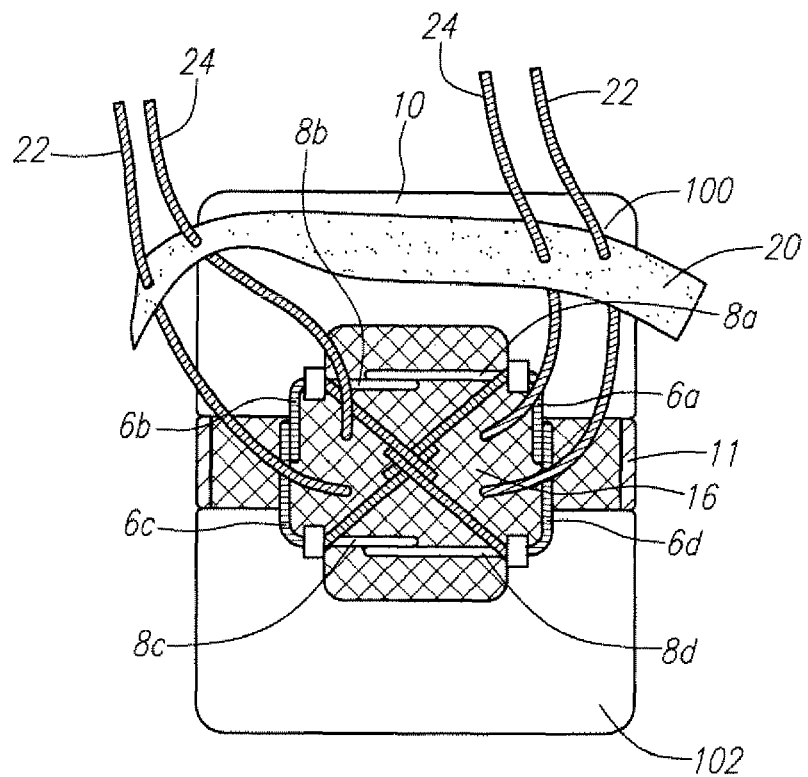
FIG. 2C illustrates an anterior view of the embodiment in FIG. 2B with an anti-adhesion cover placed over the fixation sutures and suture anchors.
Figure 2D:
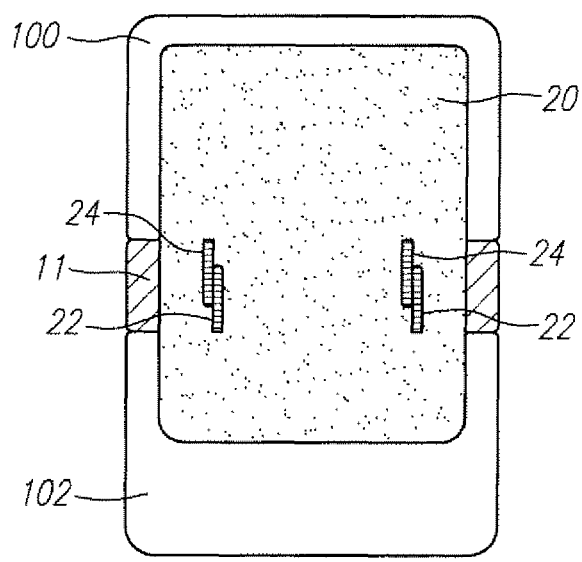
FIG. 2D illustrates an anterior view of the embodiment in FIG. 2C with an anti-adhesion cover sutured over the fixation sutures and suture anchors.

In some embodiments, the sutures and anchors can be covered with an anti-adhesion component as described in patent application 60/808,795, filed May 26, 2006, entitled "Fastening Assemblies for Disc Herniation Repair and Methods of Use," hereby expressly incorporated by reference in its entirety. For example, as shown in FIG. 2C, two connecting sutures 22 and 24 can be used to connect the anti-adhesion patch 20 to mesh patch 16. The connecting sutures 22 and 24 are passed through mesh patch 16 and anti-adhesion cover 20 and then joined together, for example by welding or any other suitable method, over the anti-adhesion cover 20 to hold the anti-adhesion cover against the vertebrae 100, 102 and annulus fibrosis 11. As shown in FIG. 2D, anti-adhesion cover 20 is sized to extend over the anchors 10a-d, mesh 16, fixation sutures 6a,b,c,d and 8a,b,c,d, the cut edges of the annulus fibrosis 111, and the cut edges of the anterior longitudinal ligament 113. In an alternative embodiment, as shown in FIG. 2H, a single connecting suture 22 can be passed through the mesh patch and anti-adhesion cover 20 and then welded, or otherwise joined, together to hold the anti-adhesion cover 20 against the vertebrae 100, 102 and annulus fibrosis 11.

Placing the stiff ends of the sutures beneath the anti-adhesion patch 20 further protects the suture welds from peeling forces due to friction from adjacent structures and helps prevent injury to delicate structures such as nerves, blood vessels, and the esophagus that lie directly over the stiff ends of the sutures. For example, as shown in FIGS. 2E-G, in an embodiment placed in the lumbrosacral spine, anti-adhesion component 20 lies between the incised portion of the spine, including the exposed portions of the suture anchors 10a,c and sutures 6a,c and 8a,c and the mesh patch 16, and the great vessels, including a portion of the aorta 30, a portion of the vena cava 32, portions of the iliac arteries 34, portions of the iliac veins 36. In some embodiments, the anti-adhesion component 20 further covers a portion of annulus fibrosis 11 and upper and lower vertebrae 100, 102. Welded sutures 22, 24 on the anterior side of anti-adhesion cover 20, holding anti-adhesion cover 20 against annulus fibrosis 11. The sutures 22, 24 that hold the anti-adhesion cover 20 against the annulus fibrosis 11 are more flexible and have a smaller diameter than the fixation sutures therefore peeling forces or injury to the adjacent structures is not an issue. Similarly, in cervical embodiments of the invention, the anti-adhesion component lies between the exposed portions of the suture anchors and sutures and the esophagus. In some embodiments, the anti-adhesion component 20 can extend further over the adjacent discs of the spine.

The anti-adhesion cover could be a piece of ePTFE attached to a portion of the mesh device and/or the fixation sutures. The anti-adhesion cover could also be made of Sepratfilm autograft, allograft, or xenograft tissues such as acellular dermis, swine intestinal submucosa, ligaments, facia, or tendon. Alternatively, the device may include a single component made of autograft, allograft, or xenograft tissues such as acellular dermis, swine intestinal submucosa, ligaments, facia, or tendon. The anti-adhesion cover may be attached to a portion of the mesh patch or device in a contracted configuration, where the anti-adhesion component is capable of being opened into an expanded configuration. The anti-adhesion component may be attached to a center portion of the mesh patch or at least one edge of the mesh patch. In the contracted configuration, the anti-adhesion cover may be bunched together, rolled, or gathered. The anti-adhesion component may be held in the contracted configuration by one or more sutures constraining element.

Figure 3A:
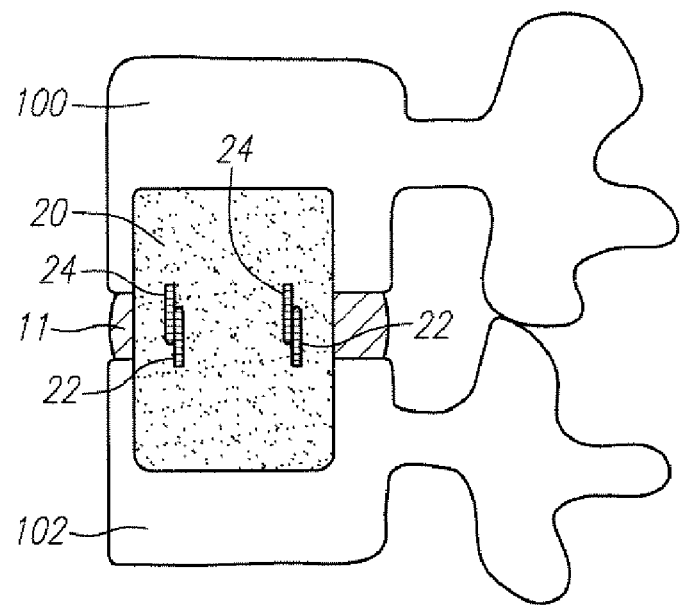
FIG. 3A illustrates is a lateral view of the spine and an alternative embodiment of the invention drawn in FIG. 2D placed on the lateral portion of the vertebrae.
Figure 3B:
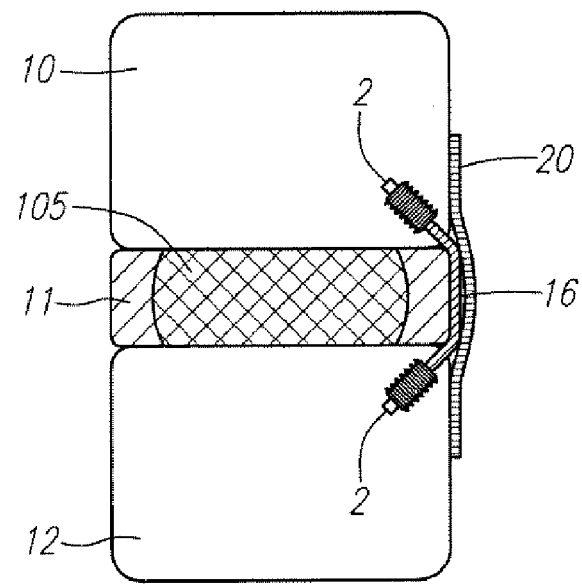
FIG. 3B illustrates an anterior view of the embodiment in FIG. 3A.

The invention may be used on the anterior, lateral, or posterior portions of the cervical, thoracic, lumbar, or sacral regions of the spine. For example, in an alternative embodiment, as shown in FIGS. 3A-B, the device can be placed over the lateral aspect of the spine. For example, the suture anchors 10a,b are inserted into the lateral portion of upper and lower vertebra 100 and 102 and sutures are passed through suture anchors 10a,b and 10c,d (not shown) and arranged over an annular window in the lateral portion of the annulus fibrosis 11. An intradiscal device 105, such as a nucleus replacement (NR), bone graft, spinal cage, or TDR can be inserted into the disc space between vertebrae 100 and 102. Sutures extending from suture anchors 10,a,b,c,d are then welded together over the intradiscal space in a pattern described above in reference to FIG. 2B. Tension can be applied to the sutures prior to welding together so that the sutures apply compression to vertebrae 100, 102 as well as hold the intradiscal device 105 in place between the vertebrae 100, 102. A mesh patch 16 is placed between the annulus fibrosis 11 and the suture welds. A second set of sutures 22, 24 are threaded through mesh patch 16 and anti-adhesion cover 20 and welded together over the anterior side of anti-adhesion cover 20 to hold anti-adhesion cover 20 against mesh patch 16, which is adjacent annulus fibrosis 11.

In some embodiments, as shown in FIG. 4A-C, one or more sutures can be used to tether the spine. Tethering the immature spine enables correction of spinal deformities such as scoliosis as the spine grows. The drawings illustrate the coronal plane deformity of scoliosis. Anchors 10e-j were placed into the lateral portions of the vertebrae on the convex side 141 of the curve. In alternative embodiments of the invention, anchors 10e-j could extend through the vertebrae. A single suture, or multiple sutures, may be threaded through the head of the anchor. Sutures 6e-j from the anchors 10e-j are welded together over the convex portion of the curve, thus allowing more growth of the portions of the vertebrae on the concave side of the spine than of the portions of the vertebrae on the convex side of the spine. The treated spine straightens as it grows. The sutures can be cut at a later surgery to prevent over correction of the spine and to allow movement across the discs.

In one embodiment, as shown in FIG. 4B, the ends of the sutures are welded together over the apex of the curve in the spine. Sutures 46a from anchors 10g, 10h in the vertebrae in the center of the curve lie over a single disc while the sutures 46e,f from the anchors 10e,j in the vertebrae at the ends of the curve pass over five discs. Tension is applied to the fixation sutures before welding the sutures together. Porous mesh sleeves (not shown) may be placed over the welded sleeves. The sleeves may be contracted, like an accordion, to facilitate welding of the sutures. The sleeves may be expanded over the sutures after welding the ends of the sutures. Additionally, the mesh sleeves and fixation sutures may be covered with an anti-adhesion component (not shown). The anchors 10e-j may be placed near the anterior portions of the vertebrae to increase kyphosis of the spine with growth of the immature spine.

In an alternative embodiment, as shown in FIG. 4C sutures 56e-l from adjacent anchors 10e-l are welded to each other, i.e., suture 56e was welded to suture 56f and suture 56g was welded to suture 56h. The embodiment of the invention helps correct rotational deformities of the spine. As described with respect to FIG. 4B, the sutures may be surrounded by mesh sleeves (not shown). Alternatively, as described in respect to FIG. 2B, porous mesh (not shown) could be placed between the welded sutures and the spine. In some embodiments, the fixation sutures, anchors, and mesh components could be covered with an anti-adhesion component or anti-adhesion components.

Figure 5:
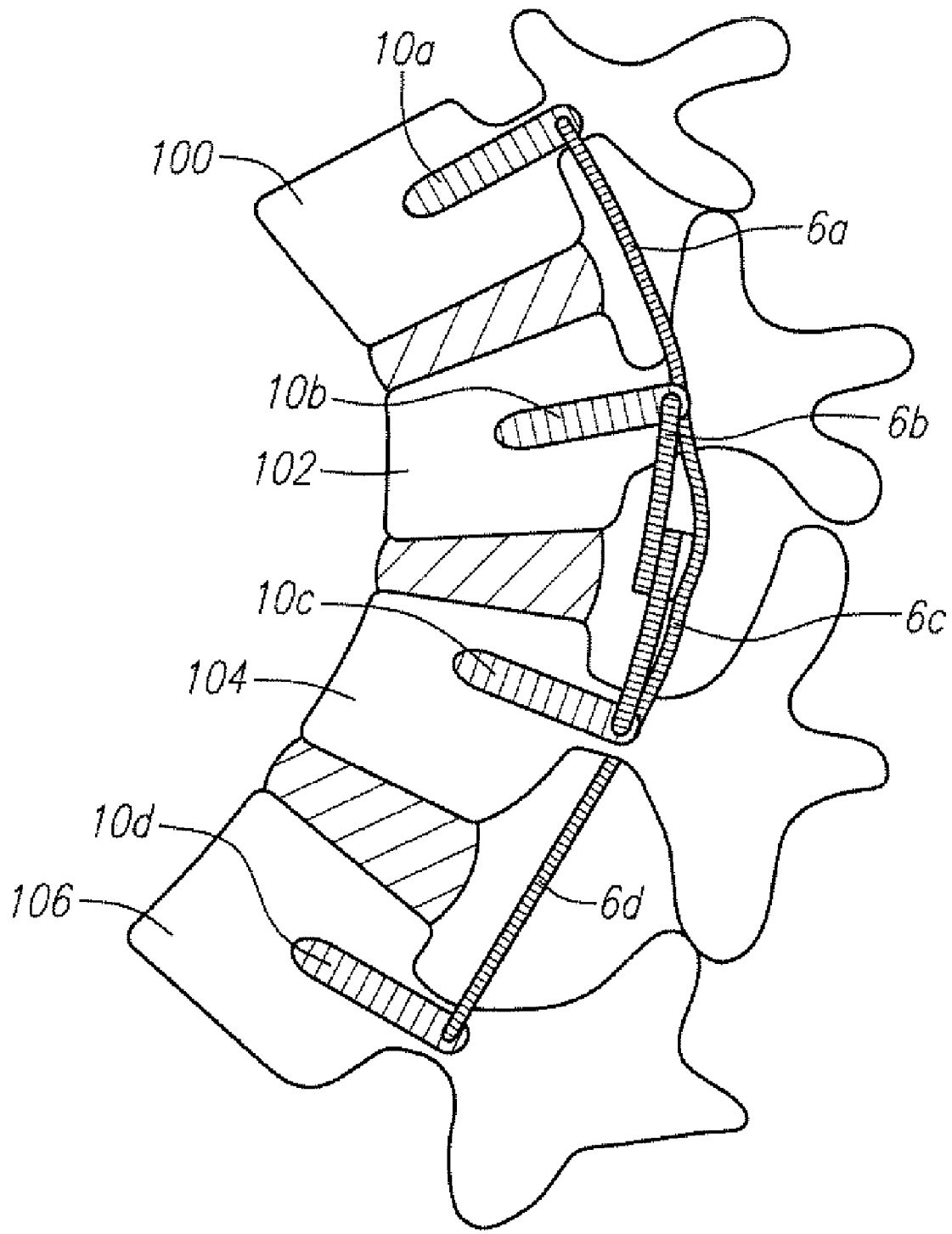
FIG. 5 is a lateral view of a portion of the spine and an alternative embodiment of the invention drawn in FIG. 4A wherein the sutures are placed on the posterior portion of the spine.

FIG. 5 is a lateral view of a portion of the spine and an alternative embodiment of the invention drawn in FIG. 4A. The sutures 6a-d from the anchors 10a-d were welded over the posterior portion of the spine. The anchors 10a-d were placed into the posterior portions of the vertebrae 100,102, 104,106. The invention may be applied to immature spines with excessive kyphosis. The posterior tether allows the spine to straighten as the spine grows.

FIG. 6A is a posterior view of the spine and an alternative embodiment of the invention. The spine was drawn with scoliosis. Sutures 6b-j were passed under the lamina of the vertebrae 100, 102, 104, 106 and 108. Sutures 6a-j were also passed around a spinal rod 33. Alternatively, the sutures 6b-j could have been passed around the transverse processes of the vertebrae. Alternatively, sutures could extend from anchors placed into the posterior portions of the vertebrae or ribs.

FIG. 6B is a posterior view of the spine and the embodiment of the invention drawn in FIG. 5A. The ends of sutures 6a-j were welded together around spinal rod 33 after applying tension to the ends of the sutures 6a-j. The embodiment of the invention could be used in spinal fusion and in fusion-less scoliosis procedures.

As discussed above, the some embodiments can be used on the anterior, lateral, or posterior portions of the cervical spine. For example, as shown in FIG. 7A suture 66 can be wrapped around the posterior portion of C1 vertebra and around the spinous process 60 of the C2 vertebra. The ends of suture 66 can then be welded together after applying tension to the ends of the suture. The embodiment may be used in C1-C2 fusion procedures. Similar procedures using the welded sutures can be performed on other vertebrae. For example as shown in FIG. 7B, two sutures 6, 8 can be placed under the lamina of C2 vertebra and the posterior portion of the C1 vertebra. The sutures 6, 8 can then be welded together after applying tension to the ends of the sutures 6,8. The embodiment of the invention may be used in C1-C2 fusion procedures, and the fusion of other vertebrae. Alternatively, as shown in FIGS. 8A-B, sutures 6 and 8 can be wrapped around and through the spinous processes 60, 62 of two cervical vertebrae and through two pieces of bone graft material 37. The sutures 6, 8 can then be welded together after applying tension to the ends of the sutures 6,8.

In some embodiments, one or more sutures can be used to hold an intradiscal device in the disc space and/or to attach prosthetic devices to the spine. For example, as shown in FIG. 9A, anchors 10a,b,c,d are placed in two adjacent vertebrae 100, 102. Sutures 6a,b,c,d are threaded through anchors 10a, b,c,d respectively. The sutures 6a,b,c,d are then passed through portions of a disc replacement device 40, for example in one embodiment the sutures 6a,b,c,d could be passed through the polyester portion of the Neodisc (NuVasive, San Diego Calif.). The disc replacement device 4U is placed in the disc space 103 between vertebrae 100, 102. Tension is applied to sutures 6a,b,c,d and the sutures 6a,b,c,d are welded together. In some embodiments the sutures may be used to hold the disc replacement device in place in disc space 103. In alternative embodiments, the sutures 6 a,b,c,d can also be used to apply compression to the vertebrae 100, 102. The arrangement of the welded sutures and the tension applied to the sutures prior to welding can be varied depending on the disc replacement device used and the function of the sutures 6a,b,c,d, i.e. whether the sutures are used to hold the disc replacement device in place or additionally to provide stabilization to the spine. For example, as shown in FIG. 9B, the sutures 6a and b can be welded together to form a first horizontal suture arm and the sutures 6c and d can be welded together to form a second horizontal suture arm to attach the intradiscal device 40 to the vertebrae 100 and 102. In an alternative embodiment, the sutures 6a,b,c,d can be welded together in an arrangement as discussed above in respect to FIG. 2B to form vertical or diagonal suture arms for holding the device 40 in the interdiscal space and for stabilizing the portion of the spine where the annulus fibrosis was excised in order to place the intradiscal device 40.

Figure 9C:
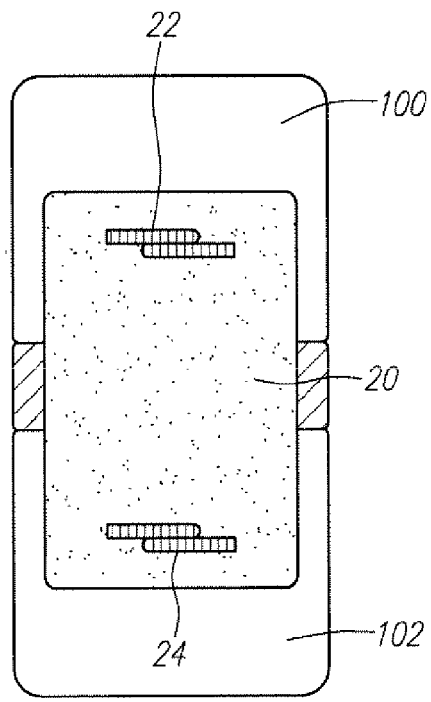
FIG. 9C is an anterior view of a portion of the embodiment of the invention drawn in FIG. 9B showing an anti-adhesion cover placed over the suture welds.

In some embodiments, as shown in FIG. 9C, an anti-adhesion component 20 can be attached to the anterior portion of the prosthetic device 40. Sutures 22, 24 can be threaded through the intradiscal device 40 and the anti-adhesion patch 20 then welded together to attach the anti-adhesion patch to the intradiscal device 40. As discussed above, the anti-adhesion component 20 prevents adhesions between the device 40 and the surrounding soft tissues. For example, anti-adhesion component 20 could be added to the disc replacement device 40, such as the Neodisc device, to prevent adhesions between the device 40 and delicate structures such as nerves, blood vessels, and the esophagus.

Figure 10A:
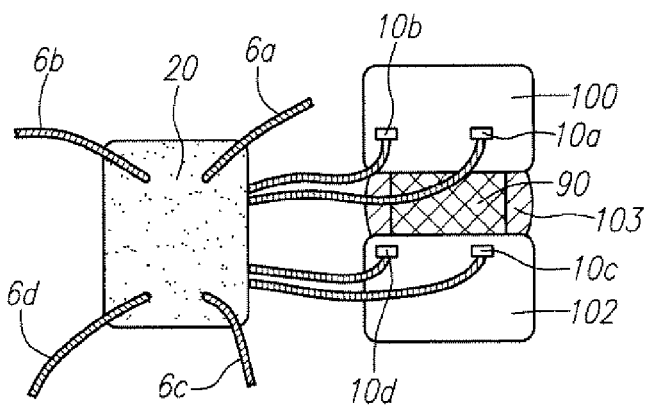
FIG. 10A illustrates an alternative embodiment of the invention using one or more sutures to hold an intradiscal device in the disc space between two vertebrae.
Figure 10B:
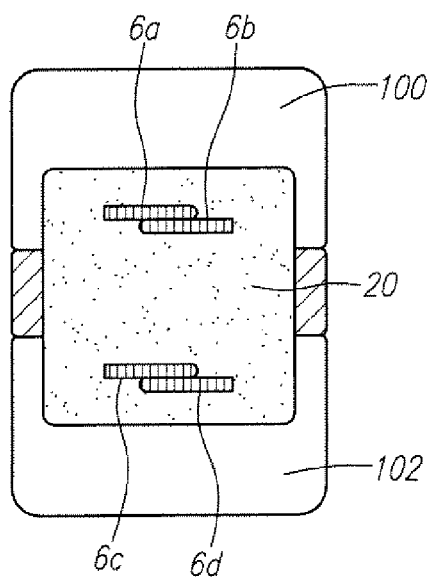
FIG. 10B is an anterior view of a portion of the embodiment of the invention drawn in FIG. 10A showing an anti-adhesion cover placed over the suture welds.

In an alternative embodiment, the sutures 6a,b,c,d can be used in conjunction with an anti-adhesion patch 20 to hold an intradiscal device 90 in place between two adjacent vertebrae 100, 102. As shown in FIG. 10A, an intradiscal device or bone graft 90 is placed between vertebrae 100, 102. Anchors 10a, b,c,d are inserted into vertebrae 100,102 and sutures 6a,b,c,d are threaded through anchors 10a,b,c,d. Sutures 6a,b,c,d are then threaded through anti-adhesion cover 20. As shown in FIG. 10B, anti-adhesion cover is positioned over vertebra 100,102 and attached to the spine with sutures 6a,b,c,d. Sutures 6a and 6b are welded to form a first horizontal suture arm and sutures 6e and d are welded together to form a second horizontal suture arm. Tension is applied to sutures 6a,b,c,d prior to welding to hold anti-adhesion cover 20 against the vertebrae 100, 102, thereby holding intradiscal device 90 in place in between vertebrae 100, 102. In some embodiments, as discussed above additional tension is applied to the sutures 6a,b,c,d to provide stabilization for the portion of the spine where the annulus fibrosis was excised in order to place the intradiscal device 90.

In some embodiments, one or more sutures can be used to repair or close defects in the soft tissue surrounding the spine such as the dura or annulus fibrosis. For example, at times the rotational, translational, and axial compression forces exceed the strength of the annular fibers resulting in tears in the annular fibers. A single event can tear one band to all the bands. Subsequent tears can connect to previous tears of a few bands resulting in a hole 120 through the entire annulus fibrosis 11 as shown in FIG. 11A. Holes through the entire annulus fibrosis can result in extrusion of the nucleus pulpous. Extrusion of the nucleus pulpous is referred to as a "herniated disc." Disc herniation can result in back pan, neck pain, arm pain, leg pain, nerve or spinal cord injury, or a combination of the above. With reference to FIG. 11B, sutures 6a,b, each having first and second ends, are placed across the defective region 120 of the annulus fibrosis 11 and first and second ends are passed through the annulus fibrosis 11 above and below the defective region 120. The sutures are preferably oriented perpendicular to the defect in the annulus. The sutures are preferably passed through the annulus and into a lumen within the tool, thus keeping the tips of the needles from injuring the nerves. For example, suture passing and welding tools from Axya Medical (Beverly, Mass.) could be used in this embodiment of the invention. Tension is applied to the sutures 6a,b to pull the defective region 120 closed and the first and second ends of each suture 6a,b are welded together. This embodiment can be used to prevent materials from leaking from the disc through the annulus fibrosis 11. For example, the invention could be used to prevent the nucleus pulpous from extruding from the disc. The invention could also be used to prevent materials that were placed into the disc from leaking out of the disc.

With reference to FIGS. 12A-B, some embodiments can be used to close a defect in the spinal dura. As shown in FIG. 12A, the dura 15 has an incision, tear, or laceration 130. As shown in FIG. 12B, sutures 6a,b are threaded through the dura 15 across the defect 130. Tension is applied to the first and second ends of the suture 6a,b and the first and second ends of each suture are welded together. In the illustrated embodiment, two sutures 6a,b are used to close the defect in the dura. In alternative embodiments, depending on the size of the tear, more or less sutures can be used to close the defect. For example, for a small tear in the dura, one suture may be adequate to repair the defect. However, if the tear is large or long, three, four or more sutures may be needed to close the tear in the dura. Welding the sutures is technically easier that tying knots in the sutures. The sutures can also be welded through smaller incisions than sutures can be tied through. Welding sutures have a lower profile than tied sutures. Lastly welds are stronger, more consistent, and less likely to allow the suture loop to lengthen than tied sutures.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for stabilizing a spinal segment, comprising the steps of:
   providing first, second, third, and fourth anchors, wherein each anchor carries a first elongate cable having first and second ends that extend from each anchor and a second elongate cable having first and second ends that extend from each anchor;
   attaching the first anchor to a first vertebra, attaching the second anchor to the first vertebra, attaching the third anchor to a second vertebra, and attaching the fourth anchor to the second vertebra; and
   attaching each of the first and second ends of the first and second elongate cables of the first anchor to create an attachment with one of the first and second ends of one of the first or second elongate cables of the second, third, and fourth anchors, attaching each of the first and second ends of the first and second elongate cables of the second anchor to create an attachment with one of the first and second ends of one of the first or second elongate cables of the first, third, and fourth anchors, attaching each of the first and second ends of the first and second elongate cables of the third anchor to create an attachment with one of the first and second ends of one of the first or second elongate cables of the first, second, and fourth anchors, attaching each of the first and second ends of the first and second elongate cables of the fourth anchor to create an attachment with one of the first and second ends of one of the first or second elongate cables of the first, second, and third anchors,
   wherein each step of attaching is accomplished by welding.

2. The method of claim 1, wherein the elongate cables are attached in the pattern of a quadrilateral having diagonal connections between vertices.

3. The method of claim 1, wherein the elongate cables are attached in the pattern of a figure-eight having left and right generally vertically extending segments and diagonal connections between upper and lower end regions of each vertically extending segment.

4. The method of claim 1, wherein the method is used to prevent excessive movement across a spinal segment.

5. The method of claim 1, wherein the method is used for annulus and spinal ligament reconstruction.

6. The method of claim 5 further comprising the step of removing at least a portion of the annulus fibrosis between a first vertebra and a second vertebra.

7. The method of claim 6, further comprising the step of inserting a total disc replacement device between a first vertebra and a second vertebra.

8. The method of claim 1, further comprising the step of removing at least a portion of the nucleus within the annulus fibrosis between a first vertebra and a second vertebra.

9. The method of claim 1, further comprising the step of replacing at least a portion of the nucleus within the annulus fibrosis between a first vertebra and a second vertebra.

10. The method of claim 1, wherein the method is used across a natural disc adjacent to a fusion construct so as to protect the adjacent natural disc.

11. The method of claim 1, wherein the method is used to treat any one or more of a natural undamaged disc, natural injured disc, a disc having a nucleus replacements, a damaged or deformed vertebrae, damaged or deformed facets joints, and other spinal injuries such as fractures, subluxations, or dislocations.

12. The method of claim 1, further comprising the step of placing a mesh patch between the elongate cables and the annulus fibrosis.

13. The method of claim 1, further comprising the step of placing an anti-adhesive patch covering over the elongate cables.

* * * * *